(12) United States Patent
Juhl Føns et al.

(10) Patent No.: US 10,513,823 B2
(45) Date of Patent: Dec. 24, 2019

(54) METHODS AND DEVICES FOR HYDROTHERMAL PRETREATMENT OF LIGNOCELLULOSIC BIOMASS

(71) Applicant: BIOFUEL TECHNOLOGY A/S, Hobro (DK)

(72) Inventors: Mogens Juhl Føns, Fårup (DK); Torben Bonde, Egå (DK)

(73) Assignee: BIOFUEL TECHNOLOGY A/S, Egå (DK)

( * ) Notice: Subject to any disclaimer, the term of this patent is extended or adjusted under 35 U.S.C. 154(b) by 427 days.

(21) Appl. No.: 15/310,606

(22) PCT Filed: Nov. 12, 2014

(86) PCT No.: PCT/DK2014/050381
§ 371 (c)(1),
(2) Date: Nov. 11, 2016

(87) PCT Pub. No.: WO2015/172787
PCT Pub. Date: Nov. 19, 2015

(65) Prior Publication Data
US 2017/0101737 A1    Apr. 13, 2017

(30) Foreign Application Priority Data

May 13, 2014    (WO) ................ PCT/DK2014/050132

(51) Int. Cl.
*D21C 1/02*    (2006.01)
*D21C 7/06*    (2006.01)
(Continued)

(52) U.S. Cl.
CPC .................................. *D21C 1/02* (2013.01);
*B01J 3/04* (2013.01); *B01J 4/005* (2013.01);
*B01J 19/006* (2013.01);
(Continued)

(58) Field of Classification Search
CPC ........ D21C 1/02; D21C 11/0007; D21C 7/12; D21C 7/06; C08H 8/00; Y02E 50/16;
(Continued)

(56) References Cited

U.S. PATENT DOCUMENTS 2,086,701 A * 7/1937 Dreyfus ................... C13K 1/02
127/1
2,542,801 A * 2/1951 De La Roza, Sr. ...... D21C 7/00
162/236

(Continued)

FOREIGN PATENT DOCUMENTS

GB          437708       * 10/1937
WO    2008/095589 A1      8/2008
(Continued)

OTHER PUBLICATIONS

International Search Report and Written Opinion for corresponding International Patent Application No. PCT/DK2014/050381 dated Sep. 21, 2015, 11 pages.

(Continued)

*Primary Examiner* — Joseph W Drodge
(74) *Attorney, Agent, or Firm* — Merchant & Gould P.C.

(57) ABSTRACT

Methods and devices are provided for hydrothermal pretreatment of lignocellulosic biomass. A mechanically simple and inexpensive vertical steam reactor is fed with biomass feedstock from the top, while pretreated material is removed from the bottom in steady-state by operation of moveable upper and lower restrictor means, which project across the reactor cross section when engaged. The vertical column of biomass is supported by the upper restrictor means. This is periodically withdrawn from the reactor cross section, permitting the column of biomass to fall by force of gravity onto the lower restrictor means. The upper restrictor means is then re-inserted, after which the lower restrictor means is withdrawn permitting a "plug" of pretreated material to be (Continued)

removed by force of gravity. Using biomass feedstock that has been compressed in a reciprocating piston press to bulk density of at least 500 kg/m3, which can be fed dry into the reactor using simple, inexpensive sluice systems and then wetted inside the reactor, this system provides comparable biomass throughput at a fraction of the cost of traditional commercial hydrothermal pretreatment systems used in "second generation" biorefining.

14 Claims, 4 Drawing Sheets

(51) Int. Cl.
 D21C 7/12 (2006.01)
 C08H 8/00 (2010.01)
 B01J 3/04 (2006.01)
 B01J 4/00 (2006.01)
 B01J 19/24 (2006.01)
 B01J 19/00 (2006.01)
 D21C 11/00 (2006.01)

(52) U.S. Cl.
 CPC ............... *B01J 19/24* (2013.01); *C08H 8/00* (2013.01); *D21C 7/06* (2013.01); *D21C 7/12* (2013.01); *D21C 11/0007* (2013.01); *C12P 2201/00* (2013.01); *Y02E 50/16* (2013.01)

(58) Field of Classification Search
 CPC ........... C12P 2201/00; C12P 7/08; C12P 7/10; C08B 1/00; C13K 1/02; C13K 1/04; C13K 1/06; C13K 1/08; B01J 3/03; B01J 3/04; B01J 4/001; B01J 4/007; B01J 4/008; B01J 2203/00; B01J 2203/06; B01J 2204/00; B01J 2204/002; B01J 2204/005; B01J 2219/00162; B01J 2219/0014; B01J 4/005; B01J 19/006; B01J 19/24; B01J 2219/00903; F16L 55/027; F16L 55/02709; F16L 55/02718; F16L 55/02736; F16L 55/02772; F15D 1/00
 USPC ................ 127/1, 36, 37; 422/112, 129, 241; 536/56, 124, 127, 128
 See application file for complete search history.

(56) References Cited

U.S. PATENT DOCUMENTS

| | | | |
|---|---|---|---|
| 2,803,540 A | 8/1957 | Durant et al. | |
| 2,858,213 A * | 10/1958 | Durant | D21C 3/24 162/17 |
| 3,432,382 A | 3/1969 | Justus | |
| 4,461,648 A | 7/1984 | Foody | |
| 5,366,558 A | 11/1994 | Brink | |
| 6,149,882 A * | 11/2000 | Guan | B01J 19/0046 422/131 |
| 8,123,864 B2 * | 2/2012 | Christensen | D21C 9/18 127/37 |
| 2004/0016525 A1 | 1/2004 | Gervais | |
| 2005/0069998 A1 | 3/2005 | Ballesteros Perdices et al. | |
| 2007/0148062 A1 * | 6/2007 | Haas | B01J 19/0006 422/603 |
| 2010/0041119 A1 * | 2/2010 | Christensen | D21C 9/18 435/162 |
| 2010/0116267 A1 * | 5/2010 | Mraz | C13K 1/02 127/1 |
| 2010/0216202 A1 * | 8/2010 | Fosbol | C13K 1/02 435/165 |
| 2010/0293847 A1 | 11/2010 | Firey | |
| 2011/0014718 A1 * | 1/2011 | Haas | B01J 19/0006 436/139 |
| 2012/0279579 A1 | 11/2012 | Simard et al. | |
| 2014/0315259 A1 * | 10/2014 | Woods | C12P 7/10 435/99 |

FOREIGN PATENT DOCUMENTS

| | | |
|---|---|---|
| WO | 2010/058285 A2 | 5/2010 |
| WO | 2011/024145 A2 | 3/2011 |
| WO | 2013/152771 A1 | 10/2013 |

OTHER PUBLICATIONS

International Search Report and Written Opinion for corresponding International Patent Application No. PCT/DK2014/050132 dated Jul. 16, 2015, 8 pages.

International Preliminary Report on Patentability for corresponding International Patent Application No. PCT/DK2014/050132 dated Nov. 17, 2015, 8 pages.

* cited by examiner

METHODS AND DEVICES FOR HYDROTHERMAL PRETREATMENT OF LIGNOCELLULOSIC BIOMASS

This application is a National Stage Application of International Application Serial No. PCT/DK2014/050381, filed 12 Nov. 2014, which claims benefit of International Application Serial No. PCT/DK2014/050132, filed 13 May 2014 and which applications are incorporated herein by reference. To the extent appropriate, a claim of priority is made to each of the above disclosed applications.

FIELD OF THE INVENTION

The invention relates to methods and devices for hydrothermal pre-treatment of lignocellulosic biomass.

BACKGROUND OF THE INVENTION

In so-called "second generation" biorefining, ethanol and/or other useful products are produced by fermentation of 5- and 6-carbons sugars derived from cellulose and hemicellulose chains of lignocellulosic biomass. In many "second generation" systems, fermentable sugars are produced through enzymatic hydrolysis of the biomass feedstock using commercially available cellulase enzyme preparations or enzyme-secreting microorganisms.

Effective enzymatic hydrolysis typically requires some form of pretreatment of the biomass feedstock in order to render cellulose chains more accessible. One particularly attractive category of pretreatment methods are so-called "hydrothermal" pretreatments. In these methods, pressurised and typically saturating steam is applied to the feedstock at temperatures between 150-220° C. corresponding to pressures between 4-23 bar, either with or without added acids, bases or other chemicals, in order to melt lignin and partially hydrolyse hemicellulose into soluble mono- and poly-saccharides, thereby improving accessibility of cellulose chains.

The capital cost of hydrothermal pretreatment systems is typically a significant component—as much as 20% or more—of total capital costs in a "second generation" biorefinery. Pressurized steam reactors suitable for large scale processing have proved expensive, in part because elaborate loading systems are required to process biomass feedstocks at ambient pressure. A variety of such loading systems have been reported, including "screw-plug" feeders, which compress biomass so as to form a pressure-tight seal while being introduced into the reactor. Other loading systems include elaborate sluice devices such as described in WO2011024145 as well as "low density" plug systems such as de-scribed in WO2010058285. Another significant component of capital cost for pressurised steam reactors is the requirement for internal agitation systems and mechanical means for continuous biomass transport.

Capital costs of the hydrothermal pretreatment system can be greatly reduced using embodiments of the vertical "plug flow" reactor described here. Isokinetic or "plug flow" transport of biomass through a pressurised steam reactor is driven by gravity alone. Effectively the only moving parts are mechanically simple "restrictor means," the periodic motions of which permit a defined quantity of pretreated biomass to be removed from the lower part of the reactor at intervals providing a steady state input of feedstock and output of pretreated biomass.

Embodiments of the invention can be applied with particular advantage in processing biomass feedstock that has been previously subject to mechanical compression using a reciprocating piston press to bulk density of at least 500 kg/m3. As described in WO2013/152771, which is hereby expressly incorporated by reference in entirety, this manner of mechanical compression to this level of bulk density produces a mechanically induced vapour expansion or "steam explosion" which greatly alters the physical properties of the material. Most notably, the capacity of lignocellulosic feedstocks to adsorb water is greatly increased, both in terms of the rate at which adsorption occurs as well the total water holding capacity. For example, as described in WO2013/152771, wheat straw subjected to "mechanical steam explosion" can typically absorb between 5 and 10 times its own weight in water.

Using feedstocks that have been compressed in this manner, there is no need to presoak the material in order to achieve an appropriate water content during pretreatment. The compressed biomass very rapidly absorbs water within the pressurised reactor. Additional water content can easily be introduced at reactor temperature and pressure in order to control the amount of water absorbed within the reactor so as to reach an optimal water content during pretreatment. Thus, a relatively large quantity of "mechanically steam exploded," compressed feedstock having low water content can be advantageously introduced into a pressurised steam reactor using a mechanically simple and inexpensive sluice loader. Furthermore, steam consumption during pretreatment can in this manner be greatly reduced. Biomass feedstocks are typically subject to hydrothermal pretreatment at water content between 65-80% by weight. See e.g. Larsen et al. (2008); Petersen et al. (2009); Kootstra et al. (2009); Larsen et al. (2012). Where hot water is added within the reactor to compressed biomass having low water content, wasteful heating of excess water is avoided. Also avoided is the unwanted increase in water content that occurs as a consequence of steam condensation associated with heating water content of the biomass feedstock up from ambient temperature.

DETAILED DESCRIPTION OF THE INVENTION

In some embodiments, the invention provides an apparatus for hydrothermal pretreatment of lignocellulosic biomass comprising a substantially vertical reactor vessel, suitable for pressurisation to between 4 and 23 bar and having a biomass inlet situated in its upper part, a biomass outlet situated in its lower part and one or more steam inlets, and upper and lower restrictor means situated in the lower part of the reactor vessel which are moveable between a retracted position in which the restrictor means do not occlude the passage of biomass through the vessel and an engaged position in which the restrictor means occlude the passage of biomass by forming a physical obstruction across the reactor vessel's cross section.

In some embodiments, the pressurisation capacity can be between 5 and 12 bar, or between 4.7 and 10 bar, or between 7 and 12 bar.

In some embodiments, the apparatus further comprises a biomass inlet sluice vessel, optionally substantially vertical, situated above the top of the substantially vertical reactor vessel, optionally in communication with a biomass feedstock input conveyor. In some embodiments, the apparatus further comprises a biomass outlet sluice vessel, optionally substantially vertical, situated beneath the bottom of the substantially vertical reactor vessel.

In some embodiments, the reactor vessel or the biomass inlet sluice vessel or both are fitted with means for injecting pressurised hot water.

In some embodiments, the restrictor means and their driving mechanism are situated within a pressurised appendix vessel that can be removed from the main reactor vessel for maintenance.

In some embodiments, the invention provides a method for hydrothermal pretreatment of lignocellulosic biomass comprising the steps of
  introducing biomass feedstock through an inlet situated in the upper part of a substantially vertical, pressurised reactor vessel in which steam pressure is maintained between 4 and 23 bar so as to maintain temperature at a level between 150-220° C. and which is fitted with upper and lower restrictor means in its lower part, in such manner that incoming feedstock lands on top of a column of biomass introduced previously that is supported inside the reactor by the upper restrictor means, followed by
  retracting the upper restrictor means to permit the column of biomass to fall downward to be supported by the lower restrictor means, followed by
  re-inserting the upper restrictor means through the column of biomass so as to support the column of biomass above the upper restrictor means, followed by
  retracting the lower restrictor means to permit the quantity of biomass that was supported by the lower restrictor means to fall downwards to an outlet situated in the lower part of the reactor vessel.

In some embodiments, the introduction of biomass feedstock is achieved in discrete batches.

In some embodiments, the method may be practiced using any embodiment of the apparatus, as described. For example, a further limitation of a method of the invention may refer to the location of restrictor means and their driving mechanism within an appendix vessel that can be removed from the main reactor vessel for maintenance.

As will be readily understood by one skilled in the art, embodiments of the method are typically practiced so as to achieve a steady-state of feedstock input and output of pretreated biomass from the reactor vessel. The vertical distance between the upper and lower restrictor means in any given reactor defines the quantity of pretreated biomass that is removed in one "batch" by one cycle of retraction and re-insertion of the restrictor means. In some embodiments, the pressurised reactor vessel can be fitted with level detector means that provides a measurement signal to inform a control process regulating the rate of feedstock input.

As is well known, steam pretreatment of lignocellulosic biomass is typically defined by the so-called "severity" of conditions. The parameter Ro, which is typically referred to as its log value, is often used in the art to define pretreatment severity, incorporating as factors both the temperature at which pretreatment is conducted as well as the residence time of biomass at that temperature: $Ro = t \, EXP\,[T-100/14.75]$, where t is residence time in minutes and T is temperature in degrees centigrade. For example, where reactor temperature is maintained at 180° C. corresponding to a saturated steam pressure of 10 bar, and where biomass feedstock is resident in that condition for 30 minutes, the pretreatment severity would be log Ro=3.84.

In embodiments of the invention, it is advantageous to achieve isokinetic "plug flow" of biomass through the vertical reactor, with gravity driven transport controlled by the periodic retraction and re-insertion of the restrictor means. Where incoming feedstock falls uniformly through the reactor vessel in order to achieve a pre-defined residence time at a pre-defined steam pressure, the output is homogeneously pretreated.

Embodiments can be practiced using a variety of different schemes for loading and un-loading biomass to and from the pressurised reactor vessel. In some embodiments, a feedstock conveyor system may feed material into the reactor through its inlet and remove pretreated material from its outlet at reactor pressure.

In some embodiments, biomass feedstock is introduced into the pressurised reactor vessel by a method comprising the steps of
  introducing biomass feedstock into a substantially vertical sluice vessel situated above a substantially vertical pressurised reactor vessel, followed by pressurisation of the sluice vessel to a pressure that is near or equal to reactor pressure, and
  opening an inlet valve situated in the upper part of the reactor vessel and introducing the biomass feedstock into the pressurised reactor vessel by gravity causing the biomass to fall from the sluice vessel through the open inlet valve.

In some embodiments, pretreated biomass is removed from the pressurised reactor vessel by a method comprising the steps of
  opening an outlet valve situated in the bottom of a substantially vertical pressurised reactor vessel and allowing pretreated biomass to fall by force of gravity through the open reactor outlet valve at reactor pressure into a substantially vertical sluice vessel situated below the reactor, followed by
  closing the reactor outlet valve and depressurising the sluice vessel to a pressure that is near or equal to ambient, followed by
  opening an outlet valve situated at the bottom of the sluice vessel and removing pre-treated biomass by action of gravity causing the material to fall through the open sluice outlet valve.

Any suitable lignocellulosic biomass can be used to practice methods of the invention, including at least wheat straw, corn stover, empty fruit bunches, rice straw, oat straw, barley straw, canola straw, rye straw, sugar cane bagasse, sorghum or sweet sorghum bagasse, and arundo. In some embodiments, methods of the invention are practiced using at least 10 kg feedstock, or at least 100 kg, or at least 500 kg.

The biomass feedstock can be advantageously pre-processed, optionally by cutting, milling or shredding to average particle size less than 3.0 cm, or less than 2.0 cm, or less than 1.0 cm, or less than 5 mm, or less than 2 mm, followed by mechanical compression using repeated compression in a reciprocating piston press to bulk density of at least 500 kg/m3, or at least 700 kg/m3, or at least 900 kg/m3, or at least 1000 kg/m3, as described in WO2013/152771.

Using repeated compression, where loose biomass feedstock is fed into a piston chamber in front of a piston which moves the loose biomass into a tubular reaction chamber in which the biomass is compressed, a mechanically induced vapour explosion or "steam explosion" is produced in the material. This greatly alters the physical properties of the feedstock, most notably greatly increasing the rate at which the material absorbs water as well as increasing its total water holding capacity.

In some embodiments this highly compressed, "mechanically steam exploded" feedstock is introduced into a pressurised reactor using a simple, small, and inexpensive sluice system. Inside the pressurised reactor, the compressed feedstock rapidly absorbs steam which condenses in the biomass as liquid water until thermal equilibrium is reached at reactor temperature. The compressed feedstock typically has a low water content less than 20% by weight. At typical reactor temperatures, for example at 180° C. corresponding to 10 bar saturated steam pressure, the water content of the compressed feedstock will only increase to about 25-35% by steam condensation associated with heating the material to reactor temperature from ambient temperature.

Optimal water content of any given compressed feedstock during pretreatment can be readily determined by one skilled in the art through routine experimentation with enzymatic hydrolysis yields and total sugar recoveries achieved with the pretreated material. In many cases, optimal water content during pretreatment may be considerably higher, possibly as high as 65%. See e.g. Modenbach and Nokes (2012); and see Allen et al. (2001).

An appropriate water content can be applied to the compressed feedstock inside a presurised reactor by simply injecting liquid water at reactor temperature, pressurised to an appropriate pressure. Injection can be advantageously achieved using nozzles that pro-vide a fine mist of liquid droplets. In some cases, where steam supply is provided by a dedicated steam generator, liquid water content of the steam provided can be in creased by avoiding application of a mist eliminator.

Compressed, "mechanically steam exploded" biomass feedstocks absorb water within the reactor at temperatures of 150° C. or higher very rapidly, typically within 1 minute, and within at most 3 minutes. By adjusting water content of the feedstock within the pressurised reactor, a very large quantity of biomass can be fed into the reactor using a small, inexpensive and mechanically simple sluice device. In contrast, where un compressed feedstock is added to a pressurised reactor at 60-65% water content, elaborate and ex-pensive sluice systems, screw plug feeders or other capital intensive loading devices are required to achieved comparable biomass throughput. Further more, when wet biomass is added to the reactor, considerable additional water content is introduced by condensation of steam associated with heating the water content to reactor temperature.

In some embodiments, the invention comprises a method for hydrothermal pretreatment of lignocellulosic biomass comprising the steps of
providing lignocellulosic biomass feedstock that has been compressed to a bulk density of at least 500 kg/m3 using a reciprocating piston press, followed by
introducing the compressed biomass feedstock into a pressurised hydrothermal pre-treatment reactor in which steam pressure is maintained at between 4 and 23 bar using a sluice system, followed by
adjusting the water content of the biomass feedstock within the pressurised reactor by introduction of pressurised liquid water.

In practicing methods of the embodiment, initial water content of the compressed biomass feedstock is typically less than 30% by weight, or less than 25%, or less than 20%, or less than 18%. Water content of the biomass is typically adjusted within the pressurised reactor to final levels which, including condensation associated with heating the biomass, are greater than 35%, or greater than 40%, or greater than 45%, or greater than 50%, or between 35% and 48%, or between 38% and 51%, or between 40% and 65%.

As used herein the term "substantially vertical" refers to a vessel that is aligned with the direction of the force of gravity such that a plumb line can be passed through it along its vertical axis.

Pressurised reactor vessels used in embodiments may have a range of sizes from bench top scale devices useful for research purposes to commercial biorefinery scale appropriate for processing 10 ton biomass/hour or more in a single vessel. Dimensions of the vessels typically fall within a range between 0.025-2.5 meters diameter and between 0.1 and 10.0 meters in height. The ratio of height to diameter is advantageously about 4:1, or between 3:1 and 5:1.

"Restrictor means" refers to a configuration of one or more physical devices that can be alternatively inserted across the cross section of a reactor vessel or retracted and that have sufficient mass and appropriate configuration so as to support a column of biomass. The appropriate mass and configuration of restrictor means can be readily determined for any given reactor size, depending on the mass of a biomass column that must be supported.

Upper restrictor means advantageously are equipped with sharpened edges, preferably points, which serve to cut through a column of biomass. These may advantageously comprise a series of individual components, which can more readily be made to pass through a biomass column and are less likely to produce accumulations of biomass that could affect "plug flow" through the reactor than a single "guillotine" surface. In some embodiments, for example, the upper restrictor means comprise a series of parallel spears having generally cylindrical shape and tapered, sharpened points at the tips which project into the reactor cross section. In some embodiments, "blades" having a flattened geometry could be used.

Lower restrictor means can be comprised by spears or by a single flat surface such as a "spade" shape.

By situating the restrictor means and their drive mechanism within a pressurised appendix vessel, it is possible to produce modular systems that can be easily removed from the pressurised reactor and replaced, permitting maintenance without significant loss of plant operation time. It is generally advantageous to maintain the restrictor means and their drive mechanism under reactor pressure because the alternative would require expensive, sensitive and high maintenance pressure seals. A readily removable appendix vessel can typically be attached to the main reactor vessel by flanges. "Sluice vessel" refers to a vessel in which biomass feedstock can be input or pretreated material removed from a pressurised reactor which operates in batch mode such that one cycle of input or output involves alternate pressurisation to a temperature at or near, meaning within 0.5 bar, of reactor pressure and depressurisation to a pressure at or near ambient.

Figure 1:
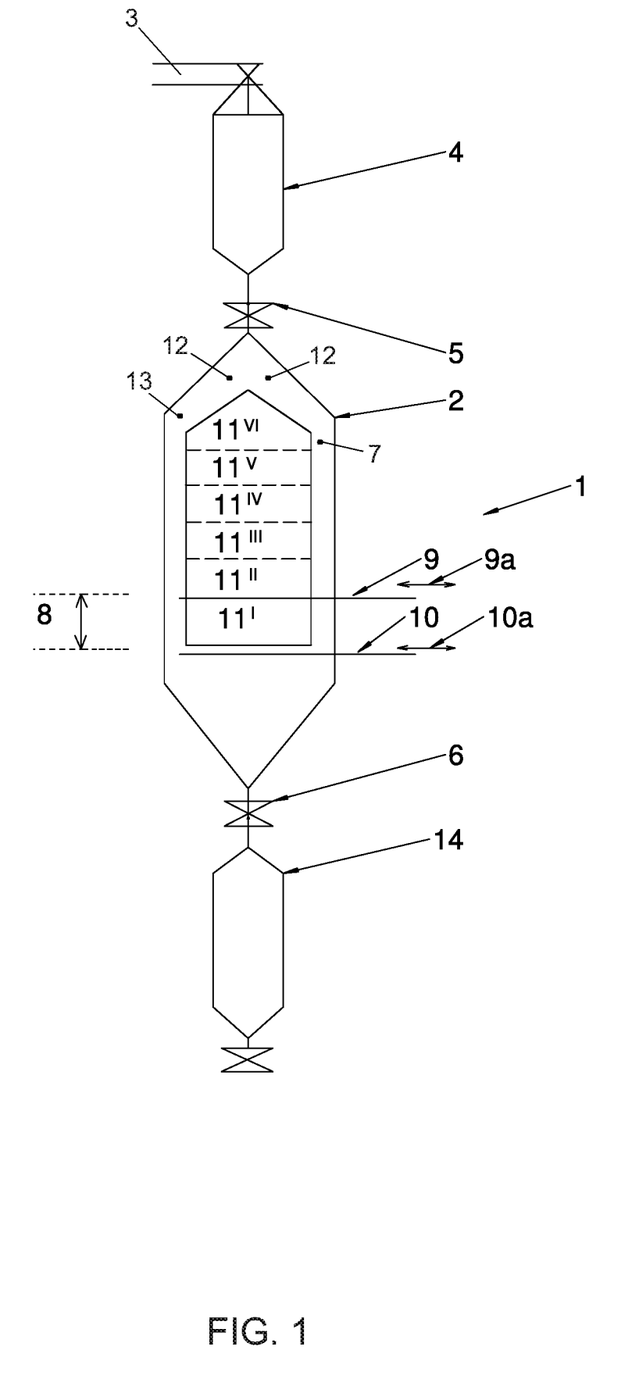
FIG. 1 shows one embodiment of an apparatus of the invention.

FIG. 1 shows one embodiment of an apparatus of the invention. The apparatus 1 comprises a substantially vertical reactor vessel 2 suitable to pressurisation to between 4 and 23 bar. The reactor vessel 2 has a biomass inlet 5 situated in its upper part and comprising an inlet valve that can be alternatively closed or open to a substantially vertical sluice vessel 4 situated above the biomass inlet 5 and a biomass outlet 6 situated in its lower part and comprising an outlet valve that can be alternatively closed or open to a substantially vertical sluice vessel 14 situated below the biomass outlet 6. The upper sluice vessel 4 is in communication with a biomass feedstock input conveyor 3. The reactor vessel 2 further comprises nozzles 12 for introduction of pressurised liquid water, at least one steam inlet 7 and a biomass level sensor 13. The reactor vessel 2 further comprises upper and lower restrictor means 9 and 10 arranged at a predetermined mutual vertical distance 8. The restrictor means are movable between a retracted position (not illustrated) and an engaged position as shown in FIG. 1. The movement of the restrictor means is illustrated by the arrows 9a and 10a.

When using the embodiment shown in FIG. 1 to practice methods of the invention, bio-mass feedstock 11 is introduced into the sluice vessel 4 by the biomass feedstock input conveyor 3 at ambient pressure. The sluice vessel 4 is then pressurised to reactor pressure and the biomass feedstock 11 introduced into the reactor vessel 2 through the inlet valve 5. Each cycle of de-pressurisation and re-pressurisation of the sluice vessel 4 introduces a batch or "plug" of biomass feedstock 11 into the reactor vessel 2. The incoming "plug" of biomass feedstock can be wetted by introduction of pressurised liquid water through nozzles 12. Steam pressure within the reactor vessel 2 can be maintained at levels between 4 and 23 bar by introduction of steam through the at least one steam inlet 7. The biomass within the reactor will have a layered structure as illustrated by the dashed lines 11$i$ through 11$vi$. Each batch or "plug" of input feedstock will thus be substantially separate. Biomass material is removed after some period of residence time in the reactor vessel 2 from the bottom, by action of the restrictor means 9 and 10. The upper restrictor means 9 is first retracted, permitting the column of biomass comprising "plugs" 11$i$ through 11$vi$ to fall down by force of gravity onto the support of the lower restrictor means 10. The upper restrictor means 9 is then re-inserted across the cross section of the reactor vessel 2, supporting the column of biomass comprising biomass "plugs" 11$ii$ through 11$vi$. The lower restrictor means 10 is then retracted, permitting the biomass "plug" 11$i$ to fall down by force of gravity through the biomass outlet valve 6 into the sluice vessel 14. By arranging the restrictor means 9 and 10 at a vertical distance 8 corresponding to the approximate thickness of a biomass "plug," residence time of biomass within the reactor vessel 2 is kept reasonably homogeneous. The biomass level sensor 13 further provides a measurement signal for control of the cycle of biomass feedstock input through the sluice vessel 4.

Figure 2:
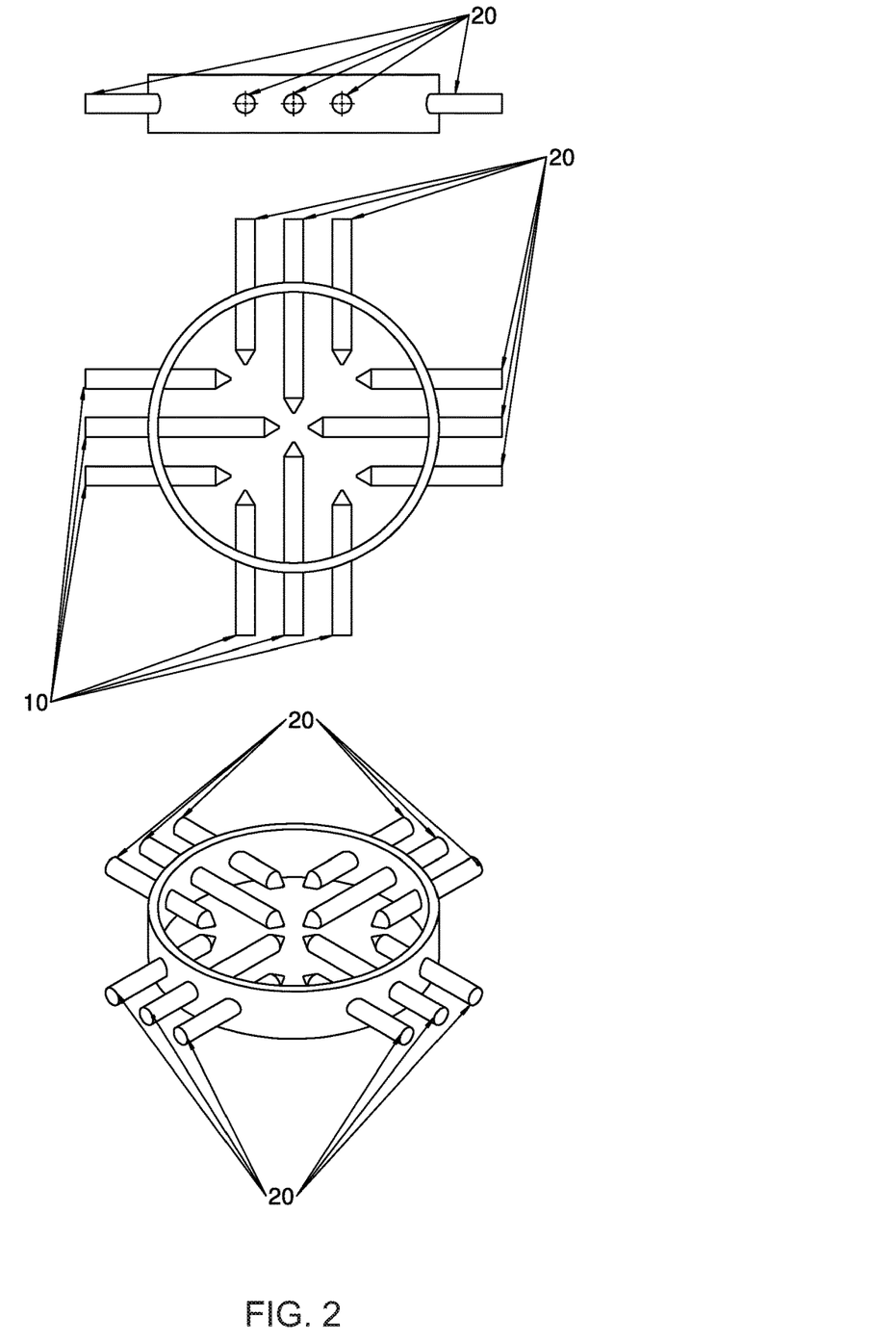
FIG. 2 shows one embodiment of restrictor means.

FIG. 2 shows one embodiment of restrictor means. In this embodiment, the restrictor means comprises a plurality of bars 20 which as explained with reference to FIG. 1 may be moved in and out of engagement as illustrated by the arrows 9a, 10a. In the embodiment illustrated in FIG. 2 the restrictor means 20 are in the shape of substantially round bars, with pointed tips. However any cross-section of the bars may be used.

Figure 3:
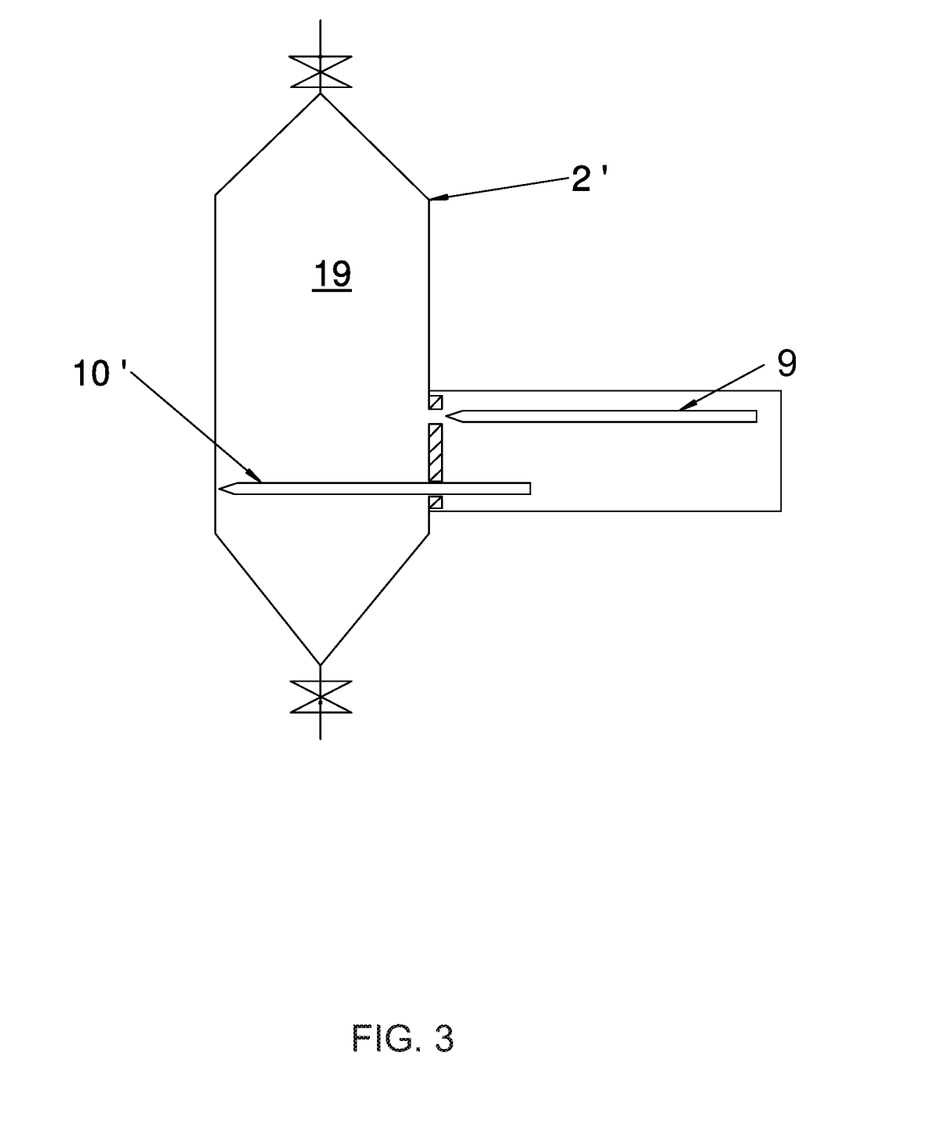
FIG. 3 shows an alternative embodiment of a reactor vessel.
Figure 4:
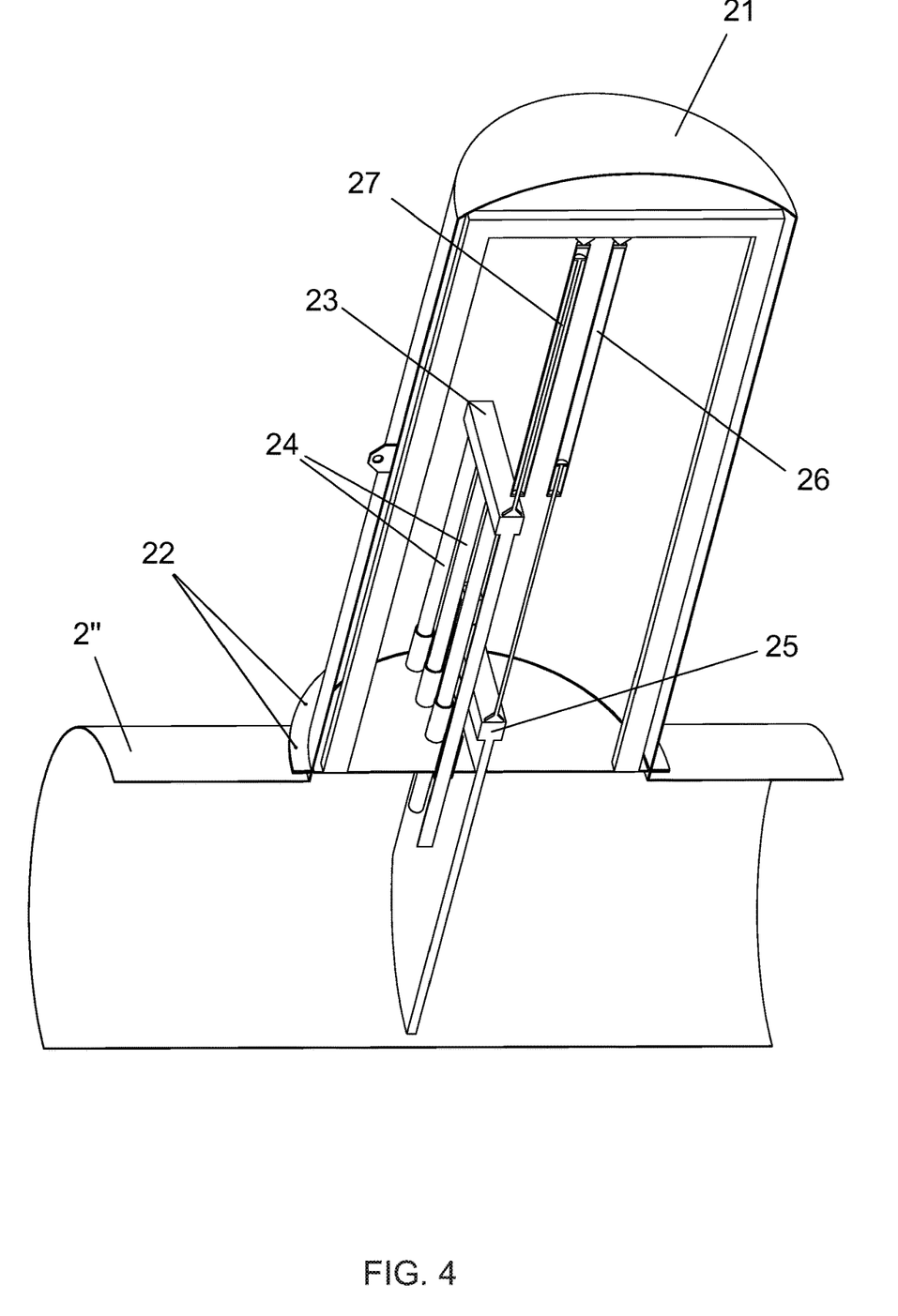
FIG. 4 shows another alternative embodiment of a reactor vessel.

FIG. 3 shows an alternative embodiment of the reactor vessel 2' where the pressurized volume 19 inside the pressurized vessel 2' has been designed to accommodate the restriction means 9', 10'. In this manner no sensitive seals or couplings need to be provided in the wall of the pressurized reactor vessel which eventually would fail and thereby reduce the service life of the reactor vessel 2' and thereby the entire apparatus. FIG. 4 shows a cross sectional view of another alternative embodiment of the reactor vessel 2". The reactor is fitted with a removable pressurised appendix vessel 21, which is attached to the main vessel by flanges 22. The appendix vessel 21 houses an upper restrictor means 23 comprising a plurality of spears 24 having tapered and sharpened points on the end which is the point of penetration of the biomass column (not shown), a lower restrictor means 25 comprising a flat spade, as well as hydraulic drive mechanisms 26 and 27 for the lower and upper 27 restrictor means respectively. The embodiments disclosed are representative only and not intended to limit the scope of the invention as defined by the claims.

REFERENCES

Allen, S. et al. "A comparison between hot liquid water and steam fractionation of corn fiber," Ind. Eng. Chem. Res. (2001) 40:2934.

Larsen, J. et al. "The IBUS process—lignocellulosic bio-ethanol close to a commercial reality," Chem. Eng. Technol. (2008) 31(5):765.

Koostra, A. et al. "Comparison of dilute mineral and organic acid pretreatment for enzymatic hydrolysis of wheat straw," Biochemical Engineering Journal (2009) 46:126.

Petersen, M. et al. "Optimization of hydrothermal pretreatment of wheat straw for production of bioethanol at low water consumption without added chemicals," Biomass and Bio-energy (2009) 33:834.

Modenbach, A. and Nokes, S. "The use of high solids loadings in biomass pretreatment—a review," Biotechnol. Bioeng. (2012) 109:1430.

Larsen, J. et al. "Inbicon makes lignocellulosic ethanol a commercial reality," Bio-mass and Bioenergy (2012) 46:36.

The invention claimed is:

1. An apparatus for hydrothermal pretreatment of lignocellulosic biomass comprising:
    a substantially vertical reactor vessel, pressure resistant to between 4 and 23 bar and having an upper part, a lower part, a biomass inlet situated in the upper part, a biomass outlet situated in the lower part, and one or more steam inlets; and
    upper and lower restrictor means situated in the lower part of the substantially vertical reactor vessel and which are moveable between a retracted position in which the upper and lower restrictor means do not occlude passage of biomass through the substantially vertical reactor vessel and an engaged position in which the upper and lower restrictor means occlude the passage of biomass by forming a physical obstruction across a cross section of the substantially vertical reactor vessel;
    wherein said upper restrictor means comprises a series of parallel spears having a generally cylindrical shape and tips which project into a cross section of the substantially vertical reactor vessel.

2. The apparatus of claim 1 further comprising a substantially vertical biomass inlet sluice vessel situated above the substantially vertical reactor vessel and in which the biomass inlet comprises an inlet valve.

3. The apparatus of claim 2 in which the biomass inlet sluice vessel is in communication with a biomass feedstock input conveyor.

4. The apparatus of claim 1 further comprising a substantially vertical biomass outlet sluice vessel situated beneath the substantially vertical reactor vessel and in which the biomass outlet comprises an outlet valve.

5. The apparatus of claim 1 further comprising means for injecting pressurised hot water situated in the upper part of the substantially vertical reactor vessel.

6. The apparatus of claim 1 in which the upper and lower restrictor means and their drive mechanism is situated within a readily removable appendix vessel pressure resistant to between 4 and 23 bar.

7. A method for hydrothermal pretreatment of lignocellulosic biomass comprising the steps of:

introducing biomass feedstock through an inlet situated in an upper part of a substantially vertical, pressurised reactor vessel in which steam pressure is maintained between 4 and 23 bar so as to maintain temperature at a level between 150-220° C. and which is fitted with upper and lower restrictor means in a lower part of the substantially vertical, pressurized reactor vessel, in such manner that incoming feedstock biomass lands on top of a column of biomass introduced previously that is supported inside the reactor by the upper restrictor means, said upper restrictor means comprises a series of parallel spears having generally cylindrical shape and tips which project into a cross section of the substantially vertical pressurized, reactor vessel, followed by retracting the upper restrictor means to permit the column of biomass to fall downwardly to be supported by the lower restrictor means, followed by re-inserting the upper restrictor means through the column of biomass so as to support the column of biomass above the upper restrictor means, followed by retracting the lower restrictor means to permit a quantity of biomass that was supported by the lower restrictor means to fall downwardly to an outlet situated in the lower part of the reactor vessel.

8. The method of claim 7 comprising a steady-state introduction of the feedstock through the inlet and removal of the biomass through the outlet.

9. The method of claim 7 wherein biomass is introduced into the pressurised reactor vessel by a method comprising the steps of:

introducing biomass feedstock into a substantially vertical sluice vessel situated above the substantially vertical pressurised reactor vessel, followed by pressurisation of the sluice vessel to a pressure that is near or equal to reactor pressure, and opening an inlet valve situated in the upper part of the reactor vessel and introducing the biomass feedstock into the pressurised reactor vessel by gravity causing the biomass to fall from the sluice vessel through the open inlet valve.

10. The method of claim 7 wherein pretreated biomass is removed from the pressurised reactor vessel by a method comprising the steps of:

opening an outlet valve situated in the bottom of a substantially vertical pressurised reactor vessel and allowing pretreated biomass to fall by force of gravity through the open reactor outlet valve at reactor pressure into a substantially vertical sluice vessel situated below the reactor, followed by closing the reactor outlet valve and de-pressurising the sluice vessel to a pressure that is near or equal to ambient, followed by opening an outlet valve situated at the bottom of the sluice vessel and removing pre-treated biomass by action of gravity causing the material to fall through the open sluice outlet valve.

11. The method of claim 7 in which the biomass feedstock comprises feedstock pre-processed by mechanical compression using repeated compression in a reciprocating piston press to bulk density of at least 500 kg/m$^3$.

12. The method of claim 11 in which water content of the biomass feedstock is adjusted within the pressurised reactor by introduction of pressurised liquid water.

13. The method of claim 12 in which water content of the biomass feedstock is adjusted within the pressurised reactor by introduction of pressurised liquid water to final levels which, including condensation associated with heating the biomass, are greater than 40% by weight.

14. The method of claim 7 wherein the upper and lower restrictor means and their drive mechanism is situated within a readily removable appendix vessel pressure resistant to between 4 and 23 bar.

* * * * *